United States Patent [19]

Verbicky

[11] 4,297,283
[45] Oct. 27, 1981

[54] CHLORINATION OF PHTHALIC ANHYDRIDE

[75] Inventor: John W. Verbicky, Scotia, N.Y.

[73] Assignee: General Electric Company, Schenectady, N.Y.

[21] Appl. No.: 195,669

[22] Filed: Oct. 9, 1980

[51] Int. Cl.$^3$ .................................................. C07D 307/89
[52] U.S. Cl. .......................... 260/346.3; 260/465 G
[58] Field of Search ......................... 260/346.3, 465 G

[56] References Cited

U.S. PATENT DOCUMENTS

| | | | |
|---|---|---|---|
| 1,935,648 | 11/1933 | Mares | 260/346.3 |
| 2,028,383 | 1/1936 | Dvornikoff | 260/346.3 |
| 2,429,985 | 11/1947 | Blume et al. | 260/346.3 |
| 3,839,401 | 10/1974 | Lavergne et al. | 260/465 G |
| 3,855,264 | 12/1974 | Watts et al. | 260/465 G |

Primary Examiner—Richard Raymond
Attorney, Agent, or Firm—Joseph T. Cohen; James C. Davis, Jr.

[57] ABSTRACT

An aromatic compound of the class of phthalic anhydride and ortho-phthalonitrile can be monochlorinated, predominantly in the 4-position, by a vapor phase reaction involving passing chlorine and the aromatic compound through a heated zone maintained at a temperature above 350° C.

7 Claims, No Drawings

CHLORINATION OF PHTHALIC ANHYDRIDE

This invention is concerned with a process for monochlorinating certain aromatic compounds. More particularly, the invention relates to a process for monochlorinating, predominantly in the 4-position, an aromatic compound selected from the class consisting of phthalic anhydride and orthophthalonitrile, which process comprises passing a mixture of chlorine and the aromatic compound, either alone or with an inert gas, through a reaction zone maintained at a temperature above 350° C.

4-chlorophthalic anhydride having the formula

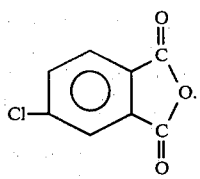

and 4-chloro ortho-phthalonitrile (from which the orthophthalic anhydride can be prepared) having the formula

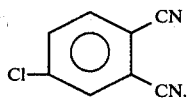

have many uses. One of the uses to which, particularly the 4-chlorophthalic anhydride can be put, is to interact the latter with a disodium phenoxide compound of the formula:

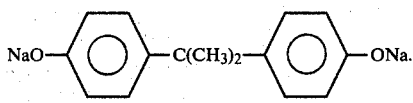

to give a dianhydride of formula:

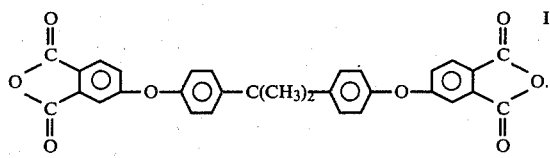

This dianhydride can then be interacted with organic diamines to make polyimide resins which have good high temperature resistance and strengths surpassing the usual engineering resins presently employed in the manufacture of products such as grill works for automobiles, housings for various electrical equipment, such as motors, stirrers, mixers, etc. Such polyimide resins are more particularly described and claimed in U.S. Pat. No. 3,847,867, issued Nov. 12, 1974 and assigned to the same assignee as the present invention.

In order to make the dianhydrides of formula IV, it is important that one of the starting materials be 4-chlorophthalic anhydride for interaction with the disodium salt of formula III. The usual methods for making the 4-chlorophthalic anhydride or the precursor, 4-chloro ortho-phthalonitrile, have involved the use of various types of relatively expensive polyvalent metal chloride catalysts, e.g., $MoCl_2$, $CoCl_2$, $FeCl_3$, etc. These catalysts are known to suffer from decomposition, loss of activity and require regeneration and special atmospheres in order to maintain their activity. In addition, it is often found that when chlorination of phthalic anhydride takes place with elemental chlorine in the melt or vapor (gaseous) phase using these polyvalent metal catalysts, excessive amounts are also formed of the 3-isomer of, for instance, either phthalic anhydride having the formula:

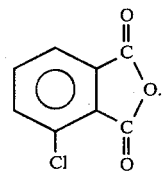

or of the phthalonitrile having the formula:

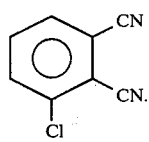

The presence of the chlorine in the 3-position rather than in the 4-position results in problems in making satisfactory polyimide resins derived, for instance, from the reaction of the chlorophthalic anhydride and the disodium phenoxide compound of formula III. If excessive amounts of the 3-chloro isomer are formed, expensive procedures must be employed to separate the 4-chloro derivative from the 3-chloro derivative, or at least reduce the concentration of the 3-chloro derivative. Moreover, the amount of 3-chloro derivative formed is usually in such high yield that it is at the expense of the 4-chloro derivative; in order to maintain the cost effectiveness of polyimide resins derived from these chlorinated aromatic compounds, it is essential that effort be expended in assuring that the 4-chloro derivative is the predominant starting product for making the dianhydride of formula IV.

Unexpectedly, I found that phthalic anhydride or phthalonitrile can be successfully monochlorinated in the vapor phase so that not only are mostly monochlorinated products obtained (as contrasted to a high proportion of dichlorinated products as prior art processes produce) but for the most part the isomer ratio of the 4-chloro isomer to the 3-chloro isomer predominates markedly in favor of the chlorine being in the 4-position. Thus, I have found that the isomer ratio can range from about 5-11 molar equivalents of the 4-position compound per molar equivalent of the 3-position compound, and by careful observance of the conditions of the reaction, good conversion of the phthalic anhydride or the phthalonitrile to the 4-chloro derivative can be realized. The position selectivity, degree of conversion, and amount of dichlorination which may be present in the reaction mixture, appear to be dependent to some degree upon the percent chlorine in the gaseous mixture with the inert gas, if the latter is used, and the temperature at which the reaction is carried out.

The reaction is advantageously performed by passing a mixture in the vapor phase of either phthalic anhydride or the phthalonitrile with gaseous chlorine, and advantageously an inert gas (such as nitrogen, helium, etc.) through a reaction chamber which is maintained at a temperature above 350° C. and below the decomposition point of the reactants or the reaction products produced, usually below 600° C., and advantageously between 350° to 475° C. Generally, the temperature should not be so high as to cause the decomposition of any of the reactants or of the reaction product nor should the temperature be so low that it interferes with the expeditious formation of the desired monochlorinated derivative in the maximum yield. The amount of chlorine used should be in a molar concentration sufficient to cause monochlorination of the aromatic compound, and advantageously in a molar excess over the aromatic compound, e.g., from 0.5 to 20 mols chlorine per mol aromatic compound.

The reaction chamber, although it does not necessarily have to be packed with any particular substance for carrying out the reaction, nevertheless, can have a packing of an inert material which provides good heat transfer for the chlorine and aromatic compound being passed through the reaction chamber. Thus, the reaction chamber which can take the form of a glass or Pyrex tube can be packed with either quartz chips or other packing well known in the art for carrying out vapor phase reactions, such as a silica packing. The important thing is that the passage of the ingredients in the vapor phase through the reaction chamber should be such that the temperature at which the gaseous chlorine and aromatic compound come in contact with each other is within the temperature range specified above.

The reaction chamber in which the chlorination takes place can be in various forms and shapes. Advantageously, the surface in contact with the chlorine and the aromatic compound should be resistant to deleterious effects of any of these reactants. For this purpose, glass or quartz surfaces are usually employed for the purpose. The reaction chamber itself can be in the form of a tube or of other configurations of such size and shape that the reaction vessel provides a sufficient residence time for the chlorine (or other halogens, for instance, bromine, iodine, which could be used in place of the chlorine) to interact with the aromatic compound to form the monochlorinated product. I have found that quartz tubes of sufficient length wherein the temperature is maintained within the required parameters, are adequate for the purpose.

It is also important to insure that the rate of passage of the vapor mixture (the gaseous phase) is such that adequate time is allowed for the chlorine and aromatic compound to interact while at the same time insuring that no more contact time is required than is practical for economically carrying out the reaction to maximize the formation of the monochlorinated aromatic compound. I have found that depending on the size of the reaction chamber (or reaction vessel) the total standard cubic feet per hour (that is the total flow of the mixture of the chlorine, and any inert gas employed, as determined by the sum of their individual flow rates) is advantageously between 0.5 and 6 cubic feet per hour. I have also found that residence times in the reactor between 8 and 50 seconds are usually sufficient to insure monochlorination of the aromatic compound in good yield without losses due to further chlorination or decomposition of any reactants or by-products. Furthermore, within these flow rates and residence times, there is a remarkable degree of selectivity of the position in which the chlorine attaches to the aromatic compound, namely, in the 4-position.

In carrying out the reaction, the chlorine gas and inert gas, if the latter is employed, is each connected to separate flow meters to control their separate flows. The gas or vapor is conducted through a single gas line, which is then passed over the surface of the molten aromatic compound. Since phthalic anhydrides and phthalonitrile have significant vapor pressures above their melting points, heating these compounds to a molten state will release vapors thereof which can be swept up with the chlorine gas and then passed through the heated reaction tube.

Generally, although no packing is usually required, the reaction vessel nevertheless is advantageously packed with inert powders, such as hollow quartz cylinders, as pointed out above, to provide means for effectively spreading the heat throughout the reaction chamber and offering a passage through which the reactants can be channeled. The end of the reaction chamber can then connect into a trapping mechanism which is cooled to, for instance, 0° C., which then enables one to cool the effluent gases, thereby depositing crystalline solids, which depending on the type of aromatic compound employed, will yield the desired product.

In order that those skilled in the art may be better understand how the present invention may be practiced, the following examples are given by way of illustration and not by way of limitation.

EXAMPLE 1

Chlorine and nitrogen gas sources were connected to separate flow meters and the flow meter effluent gases were channeled into a single gas line which connected to a gas inlet tube affixed to a 100 ml 3-neck flask containing molten phthalic anhydride at 140° C. The gas mixture was swept over the surface of the molten phthalic anhydride and then through a Pyrex elbow joint heated to 150° C. which connected to a quartz tube reaction chamber maintained at a temperature range of 360°–430° C. in a split tube furnace. The quartz tube reaction chamber was 47.5 centimeters long and had an inside diameter of 1.25 centimeters. The reaction chamber was filled along 40 centimeters of its heated length with hollow quartz cylinders approximately 0.3 centimeter in diameter and 0.6 centimeter long. The exit end of the reaction chamber was connected by means of a Pyrex elbow to a trapping flask cooled to 0° C. in an ice water bath and equipped with a water-cooled reflux condenser to further cool the effluent gases. The products were condensed from the vapor phase upon exiting the reaction chamber and were collected as white crystalline solids. The products, as pointed out above, were analyzed by liquid chromatography and the results compared with authentic samples of the chlorinated products obtained by other methods. Liquid chromatography response factors were determined for authentic samples relative to a benzophenone internal standard. The product analysis was further confirmed by gas chromatography interfaced with a mass spectrometer. The results obtained for a series of tests are given in Table I below.

TABLE I

| Test No. | Temp.$^a$ °C. | %$^b$ Cl$_2$ | Ratio I/V$^c$ | Yield$^d$ % | Flow Rate$^e$ (SCFH) | Residence Time (Sec.) |
|---|---|---|---|---|---|---|
| 1 | 420 | 37.5 | 10.75:1 | 25.5$^f$ | 4.0 | 8 |

TABLE I-continued

| Test No. | Temp.[a] °C. | %[b] Cl$_2$ | Ratio I/V[c] | Yield[d] % | Flow Rate[e] (SCFH) | Residence Time (Sec.) |
|---|---|---|---|---|---|---|
| 2 | 420 | 75.0 | 10:1 | 61.0[f] | 4.0 | 8 |
| 3 | 400 | 50.0 | 9.2:1 | 26.8[f] | 4.0 | 8 |
| 4 | 360 | 75.0 | 7.6:1 | 6.6[f] | 4.0 | 8 |
| 5 | 390 | 100.0 | 5.1:1 | 47.0[f] | 2.0 | 16 |
| 6 | 390 | 75.0 | 10.7:1 | 29.0[g] | 4.0 | 8 |
| 7 | 400 | 75.0 | 10.5:1 | 38.0[g] | 4.0 | 8 |
| 8 | 400 | 50.0 | 9.2:1 | 27.0[g] | 4.0 | 8 |
| 9 | 420 | 100.0 | 10.6:1 | 59.0[g] | 3.0 | 12 |
| 10 | 420 | 100.0 | 10.5:1 | 69.0[g] | 2.0 | 16 |
| 11 | 420 | 100.0 | 10.5:1 | 77.1[g] | 1.0 | 32 |

[a]Temperature of tube furnace enclosing reaction vessel.
[b]Percent chlorine in chlorine/nitrogen gas mixture.
[c]Composition of monochlorinated (4- or 3-isomer) products determined by liquid chromatography.
[d]Overall conversion based on recovered products and starting materials.
[e]Total flow of gases (Cl$_2$/N$_2$ mixtures) in standard cubic feet per hour.
[f]Contained less than 1 mol percent dichlorinated product.
[g]Yield of monochlorinated products only.

EXAMPLE 2

This example illustrates the chlorination of phthalonitrile. Employing the same equipment as used in Example 1, a stream of gas consisting of 66% chlorine and 34% nitrogen (by volume) was swept over molten phthalonitrile at a temperature of 180° C. and then through the quartz tube packed with quartz chips, as described above at a temperature of 420° C. and a flow rate of 3.0 SCFH with a residence of about 12 seconds. The crystalline products obtained were collected as they condensed from exiting the heated chamber. This resulted in the formation of a 66% yield of the monochlorinated phthalonitrile consisting of a ratio of 10:1 mixture of the 4-chlorophthalonitrile to the 3-chlorophthalonitrile and less than 5% of dichlorinated isomers.

It will be recognized from the above description and examples that for the first time to the knowledge of the applicant, chlorination of either phthalic anhydride or phthalonitrile, in the absence of a catalyst such as the usual polyvalent metal halide employed in the past, can be carried out to form unexpectedly good yields of the more desirable 4-chloro-substituted aromatic compound if one employs temperatures within the parameters heretofore mentioned. In addition to being able to operate without the need of catalysts for the chlorination reaction with the attendant disadvantages in using catalysts (such as loss of activity, regeneration, cost of catalyst, etc.), one also finds that the amount of dichlorinated product, whether is is the 4,5- or the 3,5-isomer of the phthalonitrile or phthalic anhydride is in relatively low quantities, thus further reducing the processing required of the reaction product to obtain as pure as possible 4-chloro derivative.

Attempts have been made in the past to chlorinate phthalic anhydride in the absence of a catalyst, but at lower temperatures (e.g., about 235° C.) no chlorination took place. It remained for the applicant to discover that by raising the temperature within a range which is practical for commercial purposes, and even in the absence of any catalyst, good yields and good conversion of the aromatic compound to the 4-chloro isomer were obtainable, with a minimum of dichlorinated products to contaminate the more desirable 4-chloro derivative.

It will of course be understood by those skilled in the art that in addition to the conditions recited and the inert atmosphere used in the foregoing examples, other conditions and other inert atmospheres can be employed within the scope of the invention. In those instances where the inert gas is omitted and the chlorine is used by itself, good results are obtained suitable in most commercial applications. The addition of inert gas provides for a better control of the flow rate and temperature, while significantly reducing the formation of undesirable by-products resulting from the oxidation caused by the chlorine gas itself coming in contact with either the phthalic anhydride or the phthalonitrile. It should however be clearly understood that the invention embraces both the absence or use of a diluent inert gas as the foregoing examples clearly illustrate.

What I claim as new and desire to secure by Letters Patent of the United States is:

1. The process for chlorinating phthalic anhydride to produce a predominantly monochlorinated compound containing a single chlorine in the 4-position so that the molar ratio of chlorine in the 4-position as contrasted to chlorine in the 3-position ranges from 5 to 11 molar equivalents of the former per molar equivalent of the 3-position compound, which process comprises passing chlorine and phthalic anhydride in the vapor phase with an inert gas, in the absence of a chlorination catalyst, through a reaction chamber maintained at a temperature above 350° C., but below 600° C., and thereafter isolating the 4-substituted phthalic anhydride.

2. The process as in claim 1 wherein the reaction chamber is packed with hollow quartz cylinders for thermal transfer.

3. The process as in claim 1 wherein nitrogen gas is used simultaneously with the chlorine gas.

4. The process as in claim 1 wherein the reaction chamber is filled with quartz chips.

5. The process as in claim 1 wherein the volume percent of chlorine in the mixture of chlorine and the inert gas ranges from 25-100%, based on the total volume of the chlorine and the inert gas, employing a sufficient molar concentration of the chlorine to cause monochlorination of the aromatic compound.

6. The process as in claim 1 wherein the aromatic compound is phthalic anhydride.

7. The process as in claim 1 wherein the aromatic compound is phthalonitrile.

* * * * *